(12) United States Patent
Fischer et al.

(10) Patent No.: US 11,124,513 B2
(45) Date of Patent: Sep. 21, 2021

(54) AVIBACTAM FREE ACID

(71) Applicant: Sandoz AG, Basel (CH)

(72) Inventors: Michael Fischer, Kundl (AT); Andreas Lechner, Kundl (AT); Brigitte Staggl, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/328,117

(22) PCT Filed: Aug. 25, 2017

(86) PCT No.: PCT/EP2017/071471
§ 371 (c)(1),
(2) Date: Feb. 25, 2019

(87) PCT Pub. No.: WO2018/037124
PCT Pub. Date: Mar. 1, 2018

(65) Prior Publication Data
US 2019/0185473 A1 Jun. 20, 2019

(30) Foreign Application Priority Data
Aug. 26, 2016 (EP) .................................. 16185913

(51) Int. Cl.
*A61K 31/4188* (2006.01)
*A61K 31/439* (2006.01)
*A61P 31/04* (2006.01)
*C07D 471/08* (2006.01)

(52) U.S. Cl.
CPC ............ *C07D 471/08* (2013.01); *A61P 31/04* (2018.01); *C07B 2200/13* (2013.01)

(58) Field of Classification Search
CPC ... A61K 31/4188; A61K 31/439; A61P 31/04; C07D 471/08
See application file for complete search history.

(56) References Cited

U.S. PATENT DOCUMENTS 7,112,592 B2 9/2006 Lampilas et al.

FOREIGN PATENT DOCUMENTS

| CN | 106699756 A | 5/2017 |
|---|---|---|
| WO | 2002010172 A1 | 2/2002 |
| WO | 2011042560 A1 | 4/2011 |
| WO | 2012172368 A1 | 12/2012 |
| WO | 2014135930 A1 | 9/2014 |
| WO | 2017025526 A1 | 2/2017 |

OTHER PUBLICATIONS

Database Chemcats, Chemical Abstracts Service, Columbus, Ohio, Feb. 23, 2015.
International Search Report and Written Opinion for PCT/EP2017/071471, dated Dec. 18, 2017, 20 pages.
New Drug Application (NDA) 206494, Submission Suppl-1: Labeling-Package Insert AVYCAZ, Sep. 2, 2015, pp. 1-20.

*Primary Examiner* — Brenda L Coleman
(74) *Attorney, Agent, or Firm* — Luedeka Neely Group, P.C.

(57) ABSTRACT

The present invention relates to avibactam free acid, a method for preparing avibactam free acid and a method for preparing avibactam sodium by further reacting avibactam free acid. The invention further refers to a pharmaceutical composition comprising avibactam free acid, one or more alkaline sodium salt(s) and one or more beta-lactam antibiotic(s). The pharmaceutical composition of the present invention can be used as medicament, in particular for treatment and/or prevention of bacterial infections.

14 Claims, 8 Drawing Sheets

AVIBACTAM FREE ACID

This application is a Section 371 national phase entry of PCT application PCT/EP2017/071471, filed Aug. 25, 2017. This application also claims the benefit of the earlier filing date of European patent application 16185913.7, filed Aug. 26, 2016.

FIELD OF THE INVENTION

The present invention relates to avibactam free acid, a method for preparing avibactam free acid and a method for preparing avibactam sodium by further reacting avibactam free acid. The invention further refers to a pharmaceutical composition comprising avibactam free acid, one or more alkaline sodium salt(s) and one or more beta-lactam antibiotic(s). The pharmaceutical composition of the present invention can be used as medicament, in particular for treatment and/or prevention of bacterial infections.

BACKGROUND OF THE INVENTION

The IUPAC name of avibactam is [(2S,5R)-2-carbamoyl-7-oxo-1,6-diazabicylco[3.2.1]octan-6-yl] hydrogen sulfate. Avibactam is represented by the following chemical structure according to Formula (I):

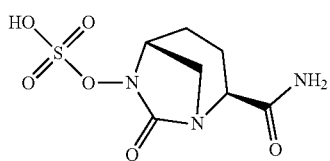

Formula (I)

Avibactam is a non-beta-lactam beta-lactamase inhibitor which is reported to have in itself no antibacterial activity at clinically relevant doses. However, avibactam protects beta-lactam antibiotics from degradation by beta lactamase enzymes and therefore maintains the antibacterial activity of beta-lactam antibiotics. It is therefore useful in conjunction with beta-lactam antibiotics for the treatment of bacterial infections.

WO 02/10172 A1 describes a synthesis pathway for avibactam sodium, which is obtained by subjecting the avibactam tetrabutylammonium salt to an ion exchange resin (DOWEX 50WX8 sodium form). Albeit mentioning also avibactam in form of the free acid, said document does neither provide a method for its preparation let alone any analytical data of avibactam free acid.

WO 2012/172368 A1 describes an alternative method of preparing avibactam sodium without the need of an ion exchange resin. According to the document, avibactam sodium can be obtained by reacting avibactam tetrabutylammonium salt with sodium 2-ethylhexanoate. Again no disclosure of avibactam free acid and its preparation is provided.

However, it was found by the inventors of the present invention that the chemical purity of the obtained avibactam sodium is solely determined by the chemical purity of the employed tetrabutylammonium salt, because the process according to WO 2012/172368 possesses no purification effect.

Hence, one objective of the present invention was the provision of an improved process for the preparation of avibactam sodium, in particular a process which allows for the preparation of highly pure avibactam sodium regardless of the quality of the applied avibactam tetrabutylammonium salt.

In addition, WO 2011/042560 A1 refers to crystalline forms of avibactam sodium. For example, WO 2011/042560 A1 discloses anhydrous forms B and D as well as hydrated forms A and E. In addition, according to the application (page 3, lines 6 to 7) a fifth form designated "form C" has been observed but only as a mixture with form A. Specifically, WO 2011/042560 A1 explicitly states that "Form C is not isolated as a pure form but is obtained in a mixture with one or more other forms, in particular Form A" (page 12, lines 5-7). However, the application does not provide any teaching on how to prepare any such mixture.

Finally, also WO 2014/135930 A1 discloses a crystalline form of avibactam sodium characterized by powder X-ray diffraction. According to the peak list provided on page 6 and the corresponding powder X-ray diffractogram displayed in FIG. 1 of said application this solid can be assigned to a mixture comprising form B and form D of WO 2011/042560 A1.

WO 2017/025526 relates to crystalline form C of avibactam sodium, especially in polymorphically pure or essentially polymorphically pure form as well as to an industrially applicable, reliable and robust process for its preparation and to pharmaceutical compositions thereof. This document represents the first disclosure for the reliable preparation and isolation of polymorphically pure form C of Avibactam sodium.

It is well-known by the skilled person that upon temperature stress or under acidic or basic conditions hydrated forms often tend to hydrolyze. Hydrates are also prone to dehydration, for example, they readily lose their water when subjected to dry conditions and/or increased temperatures. For example, WO 2011/042560 A1 mentions that form E tends to lose water and to hydrolyze (page 17 lines 1 to 2). It is further stated in the application that the avibactam sodium dihydrate form E is particularly stable above relative humidities of about 70%, indicating that this hydrated form is only stable in the presence of moisture. In addition, it was found that form E dehydrates to the monohydrate form A at temperatures above about 60° C. and that form A upon further temperature stress dehydrates to the anhydrous form B. This is critical as particular pharmaceutical processing steps such as milling and drying usually involve the evolution of heat and therefore may trigger solid form transformations of thermally labile forms. Hence, for pharmaceutical purposes anhydrous forms of avibactam and its pharmaceutically acceptable salts are preferred over hydrates.

However, also the anhydrous forms of avibactam sodium disclosed in WO 2011/042560 A1 suffer from certain drawbacks with regard to their physical properties and manufacturability respectively. For example it was surprisingly found by the inventors of the present invention that both forms B and D of avibactam sodium are not stable in the presence of moisture but significantly absorb water and undergo phase transformations, e.g. to hydrate form A, when subjected to increased relative humidity levels.

Besides proper physical properties, the manufacturability of a solid form determines, whether it is a feasible candidate for the preparation of a drug product. According to WO 2011/042560 A1 (page 16, lines 30 to 31) anhydrous form D was only obtained as very small crystals, making filtration difficult and slow. Hence, due to its limitations with regards to isolation, form D cannot be produced on industrial scale. Usually, bulk materials consisting of such small crystals also show unsatisfactory powder properties such as bad flowability and compaction properties. In addition, the robustness and reliability of a manufacturing process is a key criterion for physical form selection. WO 2011/042560 A1 (page 17, lines 8 to 14) for example mentions that anhydrous form B is difficult to prepare and only obtained in a very narrow range of water activity. Therefore, a reliable industrial production of anhydrous form B seems to be rather challenging according to the teaching of WO 2011/042560 A1.

A further objective of the present invention was therefore the provision of an improved form of avibactam, which is physically and chemically stable, i.e. which does not chemically degrade and/or convert to other solid forms during pharmaceutical processing and/or upon storage. An additional objective of the invention was to provide an improved form of avibactam, which possesses improved powder properties such as high bulk density, good flowability and no dusting and is thus more convenient to handle during pharmaceutical processing. It was a further objective of the present invention to provide an improved form of avibactam, which can be reliably and routinely manufactured also on industrial scale. Furthermore, it was an objective to provide a solid pharmaceutical composition comprising an improved form of avibactam, which is chemically and physically stable upon storage under various conditions e.g. at ambient conditions.

SUMMARY OF THE INVENTION

The present invention solves one or more of the aforementioned problems by providing avibactam in form of its free acid. Avibactam free acid of the present invention is of low hygroscopicity and stable against moisture and temperature stress. In addition, avibactam of the present invention shows advantageous morphology, homogenous particle size distribution and consequently is characterized by excellent powder properties such as bulk density, flowability and compactability, and shows no dusting.

Hence, in a first aspect the invention relates to [(2S,5R)-2-carbamoyl-7-oxo-1,6-diazabicylco[3.2.1]octan-6-yl] hydrogen sulfate (avibactam), preferably being present in crystalline form.

The present invention also relates to a method of preparing [(2S,5R)-2-carbamoyl-7-oxo-1,6-diazabicylco[3.2.1]octan-6-yl] hydrogen sulfate (avibactam).

The present invention also concerns a pharmaceutical composition comprising an effective and/or predetermined amount of [(2S,5R)-2-carbamoyl-7-oxo-1,6-diazabicylco[3.2.1]octan-6-yl] hydrogen sulfate (avibactam), one or more alkaline sodium salt(s) and one or more beta-lactam antibiotic(s) and to said pharmaceutical composition for use as medicament in particular for treatment and/or prevention of bacterial infections. A method for preparing said pharmaceutical composition is also subject-matter of the present invention.

It was surprisingly found, that avibactam in form of its free acid is obtained in high purity and therefore represents an excellent means for purification. E.g. when reacting avibactam tetrabutylammonium salt to avibactam free acid of the present invention and further reacting the free acid to the sodium salt, the final avibactam sodium is obtained in high chemical purity regardless the quality of the applied tetrabutylammonium salt. This is in contrast to the previously described process wherein avibactam sodium is directly prepared from the tetrabutylammonium salt, where the purity of the obtained product is directly dependent on the chemical purity of the employed tetrabutylammonium salt, said process showing no purification effect.

Hence, the present invention also relates to the use of [(2S,5R)-2-carbamoyl-7-oxo-1,6-diazabicylco[3.2.1]octan-6-yl] hydrogen sulfate (avibactam) for the preparation of avibactam salts, in particular avibactam sodium.

Finally, another aspect of the invention concerns a method for preparing avibactam sodium from [(2S,5R)-2-carbamoyl-7-oxo-1,6-diazabicylco[3.2.1]octan-6-yl] hydrogen sulfate (avibactam).

Definitions

Unless indicated otherwise the terms used herein have the following meanings:

As used herein the term "avibactam" refers to [(2S,5R)-2-carbamoyl-7-oxo-1,6-diazabicylco[3.2.1]octan-6-yl] hydrogen sulfate which can be represented by the chemical structure according to Formula (I) herein. In the present invention "avibactam" indicates the free acid form, where the hydrogen atom of the sulfuric acid group is not substituted by another kind of atom, for example by sodium or potassium.

As used herein the term "room temperature" refers to a temperature in the range of from 20 to 30° C.

The term "reflection" with regards to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately $10^3$ to $10^{20}$ atoms, whereas short-range order is over a few atoms only (see *"Fundamentals of Powder Diffraction and Structural Characterization of Materials"* by Vitalij K. Pecharsky and Peter Y. Zavalij, Kluwer Academic Publishers, 2003, page 3).

The term "essentially the same" with reference to powder X-ray diffraction means that variabilities in peak positions and relative intensities of the peaks are to be taken into account. For example, a typical precision of the 2-Theta values is in the range of ±0.2° 2-Theta. Thus, a diffraction peak that usually appears at 6.5° 2-Theta for example can appear in the range of from 6.3° to 6.7° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

The term "essentially the same" with reference to Fourier transform infrared spectroscopy means that variabilities in peak positions and relative intensities of the peaks are to be taken into account. For example, a typical precision of the wavenumbers is in the range of ±2 cm$^{-1}$. Thus, a peak that usually appears at 1820 cm$^{-1}$ can appear in the range of from 1818 to 1822 cm$^{-1}$ on most infrared spectrometers under standard conditions. Furthermore, one skilled in the art will appreciate that relative peak intensities will show inter-apparatus variability as well as variability due to degree of crystallinity, sample preparation and other factors known to those skilled in the art and should be taken as qualitative measure only.

The term "solid form" as used herein refers to any crystalline and amorphous phase of a material.

The term "form A" or "crystalline form A" as used herein refers to the crystalline monohydrate of avibactam sodium disclosed in WO 2011/042560 A1 which is characterized by having a PXRD comprising reflections at 2-Theta angles of (8.5±0.2)°, (15.3±0.2)° and (16.4±0.2)°, when measured with Cu-Kalpha$_{1,2}$ radiation having a wavelength of 0.15419 nm.

The term "form B" or "crystalline form B" as used herein refers to the crystalline form of avibactam sodium disclosed in WO 2011/042560 A1 which is characterized by having a PXRD comprising reflections at 2-Theta angles of (13.0±0.2)°, (16.5±0.2)°, (17.2±0.2)°, when measured with Cu-Kalpha$_{1,2}$ radiation having a wavelength of 0.15419 nm.

The term "form D" or "crystalline form D" as used herein refers to the crystalline form of avibactam sodium disclosed in WO 2011/042560 A1 which is characterized by having a PXRD comprising reflections at 2-Theta angles of (12.4±0.2)°, (16.2±0.2)°, (17.4±0.2)°, (17.8±0.2)°, (18.5±0.2)° and (22.2±0.2)°, when measured with Cu-Kalpha$_{1,2}$ radiation having a wavelength of 0.15419 nm.

The term "form C" or "crystalline form C" as used herein refers to the crystalline form of avibactam sodium disclosed in WO 2017/025526 A1 which is characterized by having a PXRD comprising reflections at 2-Theta angles of (6.5±0.2)°, (14.4±0.2)°, (15.5±0.2)°, (18.0±0.2)° and (19.3±0.2)°, when measured at room temperature with Cu-Kalpha$_{1,2}$ radiation having a wavelength of 0.15419 nm.

The term "about" as used herein means within 5%, more typically within 1% and most typically within 0.5% of the indicated value or range.

The term "treating bacterial infections" as used herein includes the cure, prevention and/or amelioration of conditions directly or indirectly caused by bacteria, in particular beta-lactamase producing bacteria.

The term "predetermined amount" of avibactam as used herein refers to the amount of avibactam which is present in a composition, e.g. a pharmaceutical composition, at the time of preparing said composition.

The term "effective amount" of avibactam as used herein means an amount sufficient to provide a therapeutic benefit in the treatment of a disease or disorder, or to delay or minimize one or more symptoms associated with the disease or disorder.

As used herein the term "isolated" with reference to avibactam corresponds to avibactam that is physically separated from the reaction mixture in which it is formed.

As used herein the term "plates" or "plate-like" with regards to particle or crystal shape refers to flat, tabular particles or crystals which have similar breadth and width.

The term "laths" as used herein with regards to particle or crystal shape refers to elongated, thin and blade-like particles or crystals.

The term "agitation" as used herein relates to any motion of a macroscopic constituent of a solution or suspension which is induced from outside, relative to another macroscopic constituent of the solution or suspension. The term "mechanical agitation" as used herein relates to any motion of a macroscopic constituent of a solution or suspension which is induced from outside via a device, such as shaking or stirring or sonication, relative to another macroscopic constituent of the solution. The term "stirring" as used herein relates to any motion of a macroscopic constituent of a solution or suspension which is induced from outside via a stirring device, relative to another macroscopic constituent of the solution or suspension.

DETAILED DESCRIPTION OF THE INVENTION

Different aspects of the invention are described below in further detail by embodiments, without being limited thereto. Each aspect of the invention may be described by one embodiment or by combining two or more embodiments.

In a first aspect the invention relates to [(2S,5R)-2-carbamoyl-7-oxo-1,6-diazabicylco[3.2.1]octan-6-yl] hydrogen sulfate according to Formula (I)

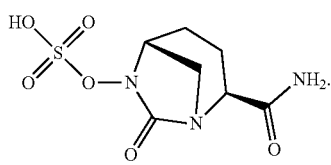

Formula (I)

In one embodiment the present invention relates to [(2S,5R)-2-carbamoyl-7-oxo-1,6-diazabicylco[3.2.1]octan-6-yl] hydrogen sulfate according to Formula (I) being present in isolated form.

In another embodiment the present invention relates to [(2S,5R)-2-carbamoyl-7-oxo-1,6-diazabicylco[3.2.1]octan-6-yl] hydrogen sulfate according to Formula (I) being present in solid form.

In a further embodiment the present invention relates to [(2S,5R)-2-carbamoyl-7-oxo-1,6-diazabicylco[3.2.1]octan-6-yl] hydrogen sulfate according to Formula (I) being present in crystalline form.

In a preferred embodiment the present invention relates to a crystalline form (Form 1) of [(2S,5R)-2-carbamoyl-7-oxo-1,6-diazabicylco[3.2.1]octan-6-yl] hydrogen sulfate according to Formula (I) characterized by having a powder X-ray diffractogram comprising reflections at 2-Theta angles of:

(9.6±0.2)°, (11.1±0.2)° and (17.4±0.2)°, or
(9.6±0.2)°, (11.1±0.2)°, (16.4±0.2)° and (17.4±0.2)°, or
(9.6±0.2)°, (11.1±0.2)°, (16.4±0.2)°, (17.4±0.2)° and (19.2±0.2)°, or
(9.6±0.2)°, (11.1±0.2)°, (16.4±0.2)°, (17.4±0.2)° (19.2±0.2)° and (22.1±0.2)°, or
(9.6±0.2)°, (11.1±0.2)°, (16.4±0.2)°, (17.4±0.2)° (19.2±0.2)°, (22.1±0.2)° and (24.2±0.2)°, or
(9.6±0.2)°, (11.1±0.2)°, (16.4±0.2)°, (16.7±0.2)°, (17.4±0.2)° (19.2±0.2)°, (22.1±0.2)° and (24.2±0.2)°, when measured with Cu-Kalpha$_{1,2}$ radiation having a wavelength of 0.15419 nm.

Figure 1:
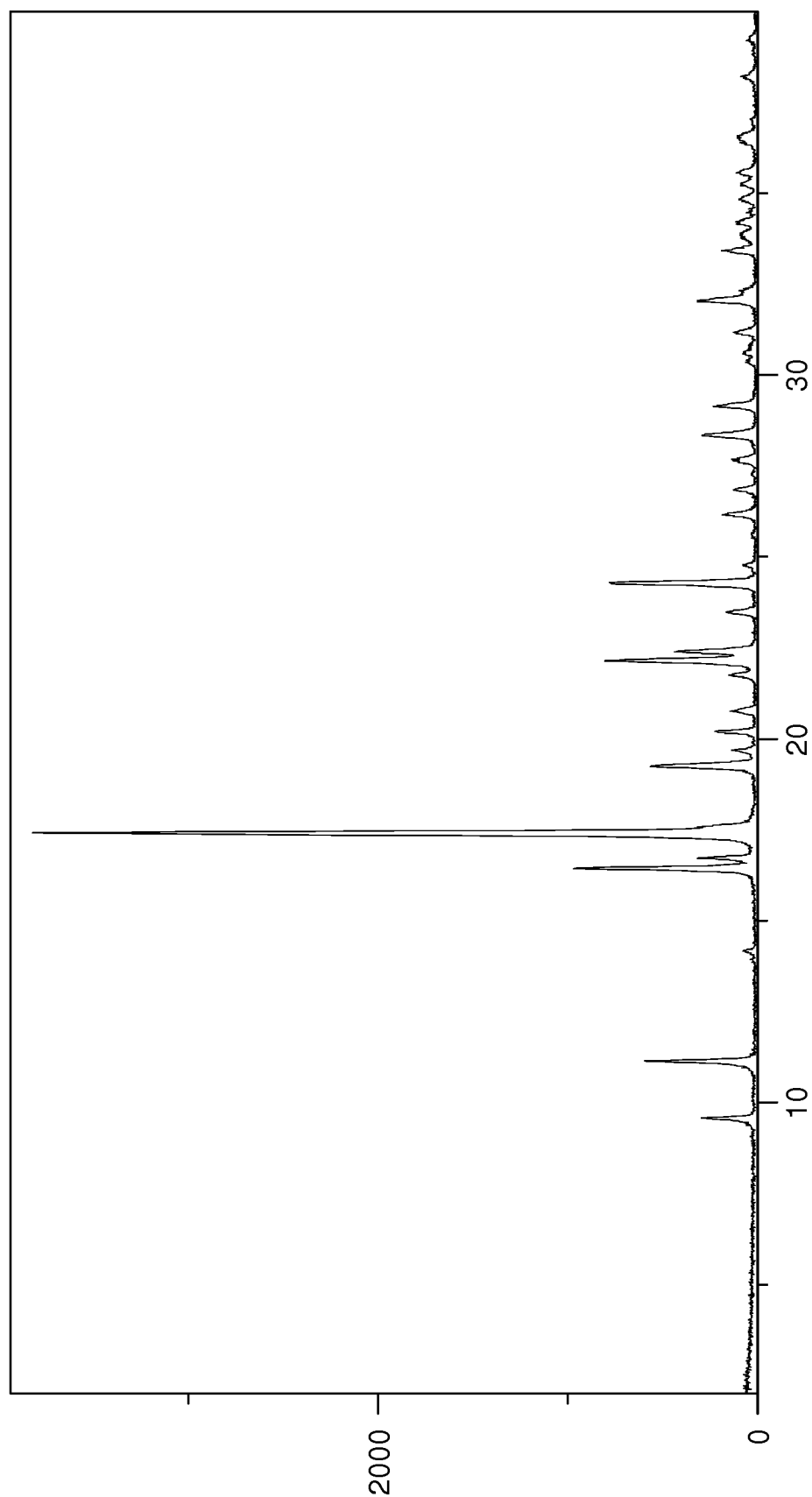
FIG. 1: illustrates a representative powder X-ray diffractogram of the crystalline form (Form 1) of avibactam according to the present invention. The x-axis shows the scattering angle in °2-theta, the y-axis shows the intensity of the scattered X-ray beam in counts of detected photons.

In still another embodiment the present invention relates to a crystalline form (Form 1) of [(2S,5R)-2-carbamoyl-7-oxo-1,6-diazabicylco[3.2.1]octan-6-yl] hydrogen sulfate according to Formula (I) characterized by having a powder X-ray diffractogram essentially the same as the one displayed in FIG. 1 of the present invention, when measured with Cu-Kalpha$_{1,2}$ radiation having a wavelength of 0.15419 nm.

In another preferred embodiment the present invention relates to a crystalline form (Form 2) of [(2S,5R)-2-carbamoyl-7-oxo-1,6-diazabicylco[3.2.1]octan-6-yl] hydrogen sulfate according to Formula (I) characterized by having a powder X-ray diffractogram comprising reflections at 2-Theta angles of:

(9.3±0.2)°, (10.1±0.2)° and (16.7±0.2)°, or
(9.3±0.2)°, (10.1±0.2)°, (16.7±0.2)° and (18.8±0.2)°, or
(9.3±0.2)°, (10.1±0.2)°, (16.3±0.2)°, (16.7±0.2)° and (18.8±0.2)°, or
(9.3±0.2)°, (10.1±0.2)°, (16.3±0.2)°, (16.7±0.2)° (18.8±0.2)° and (24.4±0.2)°, or
(9.3±0.2)°, (10.1±0.2)°, (16.3±0.2)°, (16.7±0.2)° (18.8±0.2)°, (19.5±0.2)° and (24.4±0.2)°, or
(9.3±0.2)°, (10.1±0.2)°, (16.3±0.2)°, (16.7±0.2)°, (18.8±0.2)° (19.5±0.2)°, (23.0±0.2)° and (24.4±0.2)°, when measured with Cu-Kalpha$_{1,2}$ radiation having a wavelength of 0.15419 nm.

Figure 6:
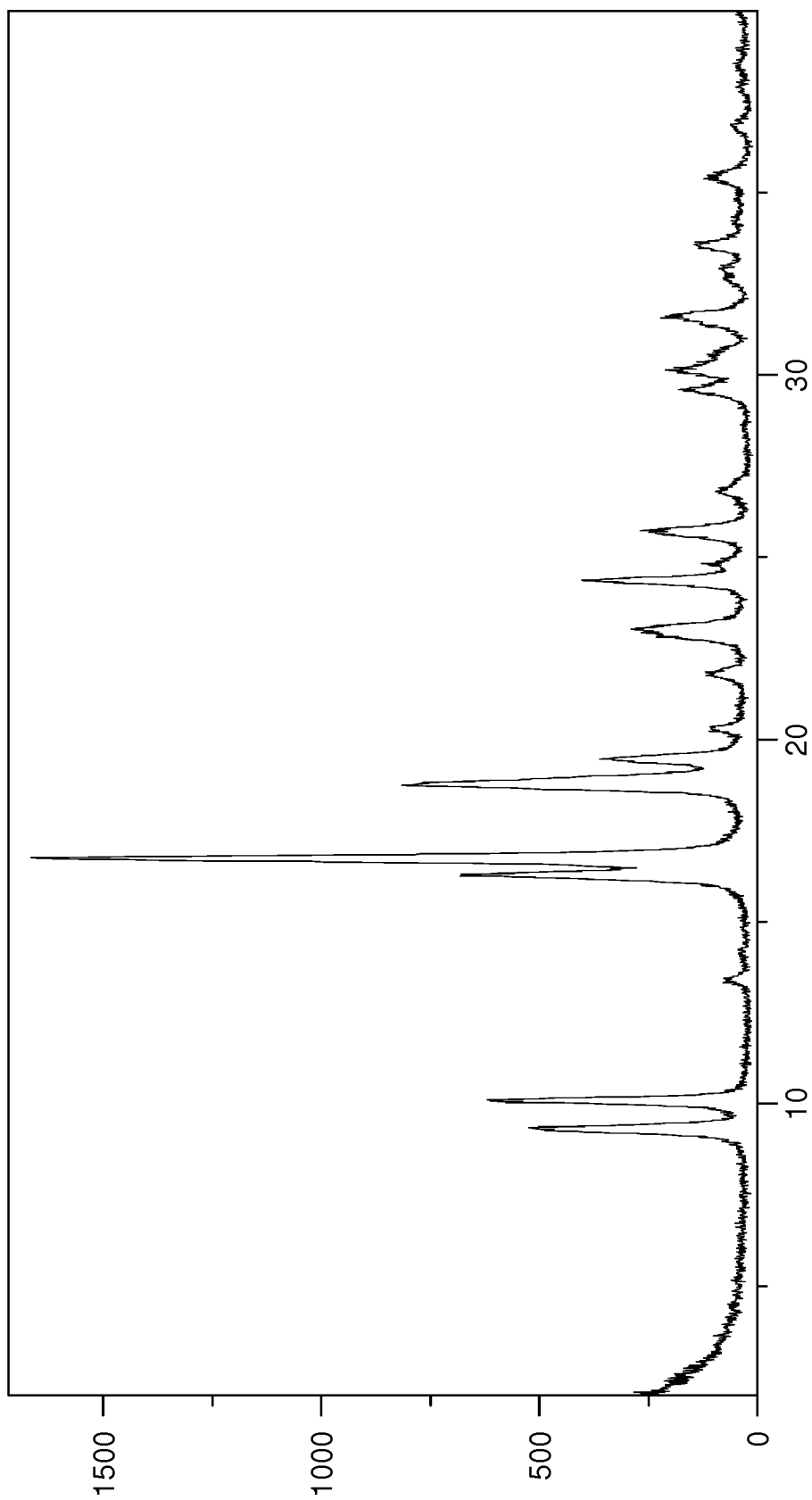
FIG. 6: illustrates a representative powder X-ray diffractogram of the crystalline form (Form 2) of avibactam according to the present invention. The x-axis shows the scattering angle in °2-theta, the y-axis shows the intensity of the scattered X-ray beam in counts of detected photons.

In still another embodiment the present invention relates to a crystalline form (Form 2) of [(2S,5R)-2-carbamoyl-7-oxo-1,6-diazabicylco[3.2.1]octan-6-yl] hydrogen sulfate according to Formula (I) characterized by having a powder X-ray diffractogram essentially the same as the one displayed in FIG. 6 of the present invention, when measured with Cu-Kalpha$_{1,2}$ radiation having a wavelength of 0.15419 nm.

In a further embodiment the present invention relates to a crystalline form (Form 1) of [(2S,5R)-2-carbamoyl-7-oxo-1,6-diazabicylco[3.2.1]octan-6-yl] hydrogen sulfate according to Formula (I) characterized by having a Fourier transform infrared spectrum comprising peaks at wavenumbers of:

(3391±2) cm$^{-1}$, (1820±2) cm$^{-1}$ and (1688±2) cm$^{-1}$, or
(3391±2) cm$^{-1}$, (3274±2) cm$^{-1}$, (1820±2) cm$^{-1}$ and (1688±2) cm$^{-1}$, or
(3391±2) cm$^{-1}$, (3274±2) cm$^{-1}$, (1820±2) cm$^{-1}$, (1688±2) cm$^{-1}$ and (1619±2) cm$^{-1}$, or
(3391±2) cm$^{-1}$, (3274±2) cm$^{-1}$, (3214±2) cm$^{-1}$, (1820±2) cm$^{-1}$, (1688±2) cm$^{-1}$ and (1619±2) cm$^{1}$, or
(3391±2) cm$^{-1}$, (3274±2) cm$^{-1}$, (3214±2) cm$^{-1}$, (1820±2) cm$^{-1}$, (1688±2) cm$^{-1}$
(1619±2) cm$^{-1}$ and (1304±2) cm$^{-1}$, or
(3391±2) cm$^{-1}$, (3326±2) cm$^{-1}$, (3274±2) cm$^{-1}$, (3214±2) cm$^{-1}$, (1820±2) cm$^{-1}$,
(1688±2) cm$^{-1}$, (1619±2) cm$^{-1}$ and (1304±2) cm$^{-1}$, or
(3391±2) cm$^{-1}$, (3326±2) cm$^{-1}$, (3274±2) cm$^{-1}$, (3214±2) cm$^{-1}$, (1820±2) cm$^{-1}$,
(1688±2) cm$^{-1}$, (1619±2) cm$^{-1}$, (1304±2) cm$^{-1}$ and (1241±2) cm$^{-1}$, or
(3391±2) cm$^{-1}$, (3326±2) cm$^{-1}$, (3274±2) cm$^{-1}$, (3214±2) cm$^{-1}$, (1820±2) cm$^{-1}$,
(1688±2) cm$^{-1}$, (1619±2) cm$^{-1}$, (1304±2) cm$^{-1}$, (1241±2) cm$^{-1}$ and (1054±2) cm$^{-1}$, when measured with a diamond ATR cell.

Figure 2:
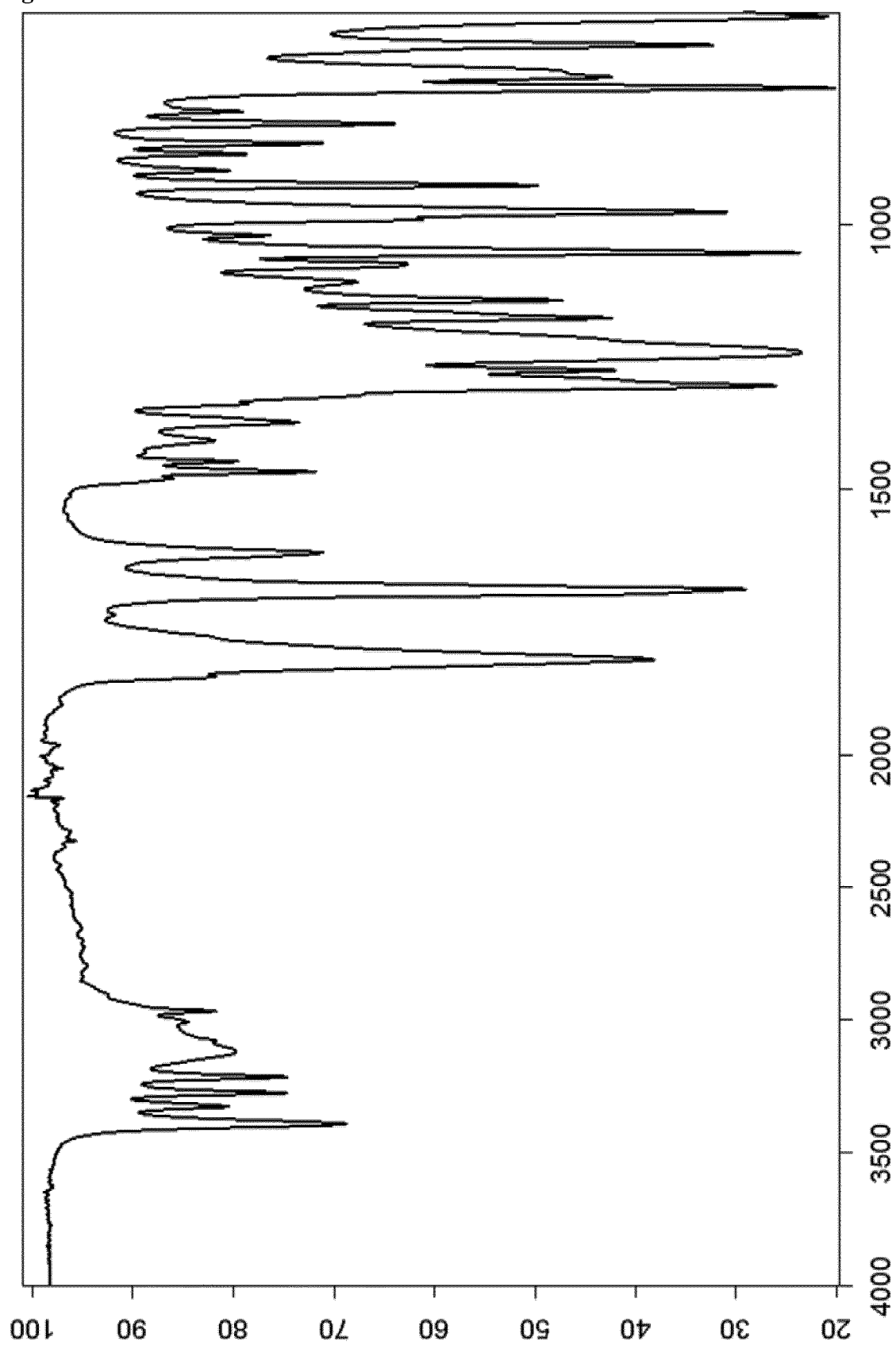
FIG. 2: illustrates a representative Fourier transform infrared spectrum in transmission mode of the crystalline form (Form 1) of avibactam according to the present invention. The x-axis shows the frequency in wavenumbers (cm$^{-1}$), the y-axis shows the relative intensity of the peaks in percent (%).

In one embodiment the present invention relates to a crystalline form (Form 1) of [(2S,5R)-2-carbamoyl-7-oxo-1,6-diazabicylco[3.2.1]octan-6-yl] hydrogen sulfate according to Formula (I) characterized by having a Fourier transform infrared spectrum essentially the same as the one displayed in FIG. 2 of the present invention, when measured with a diamond ATR cell.

In a further embodiment the present invention relates to a crystalline form (Form 2) of [(2S,5R)-2-carbamoyl-7-oxo-1,6-diazabicylco[3.2.1]octan-6-yl] hydrogen sulfate according to Formula (I) characterized by having a Fourier transform infrared spectrum comprising peaks at wavenumbers of:

(3403±2) cm$^{-1}$, (1825±2) cm$^{-1}$ and (1686±2) cm$^{-1}$, or
(3403±2) cm$^{-1}$, (3277±2) cm$^{-1}$, (1825±2) cm$^{-1}$ and (1686±2) cm$^{-1}$, or
(3403±2) cm$^{-1}$, (3277±2) cm$^{-1}$, (1825±2) cm$^{-1}$, (1686±2) cm$^{-1}$ and (1616±2) cm$^{-1}$, or
(3403±2) cm$^{-1}$, (3277±2) cm$^{-1}$, (3214±2) cm$^{-1}$, (1825±2) cm$^{-1}$, (1686±2) cm$^{-1}$ and (1616±2) cm$^{-1}$, or
(3403±2) cm$^{-1}$, (3277±2) cm$^{-1}$, (3214±2) cm$^{-1}$, (1825±2) cm$^{-1}$, (1686±2) cm$^{-1}$
(1616±2) cm$^{-1}$ and (1297±2) cm$^{-1}$, or
(3403±2) cm$^{-1}$, (3326±2) cm$^{-1}$, (3277±2) cm$^{-1}$, (3214±2) cm$^{-1}$, (1825±2) cm$^{-1}$,
(1686±2) cm$^{-1}$, (1616±2) cm$^{-1}$ and (1297±2) cm$^{-1}$, or
(3403±2) cm$^{-1}$, (3326±2) cm$^{-1}$, (3277±2) cm$^{-1}$, (3214±2) cm$^{-1}$, (1825±2) cm$^{-1}$,
(1686±2) cm$^{-1}$, (1616±2) cm$^{-1}$, (1297±2) cm$^{-1}$ and (1251±2) cm$^{-1}$, or
(3403±2) cm$^{-1}$, (3326±2) cm$^{-1}$, (3277±2) cm$^{-1}$, (3214±2) cm$^{-1}$, (1825±2) cm$^{-1}$, (1686±2) cm$^{-1}$, (1616±2) cm$^{-1}$, (1297±2) cm$^{-1}$, (1251±2) cm$^{-1}$ and (1053±2) cm$^{-1}$, when measured with a diamond ATR cell.

Figure 7:
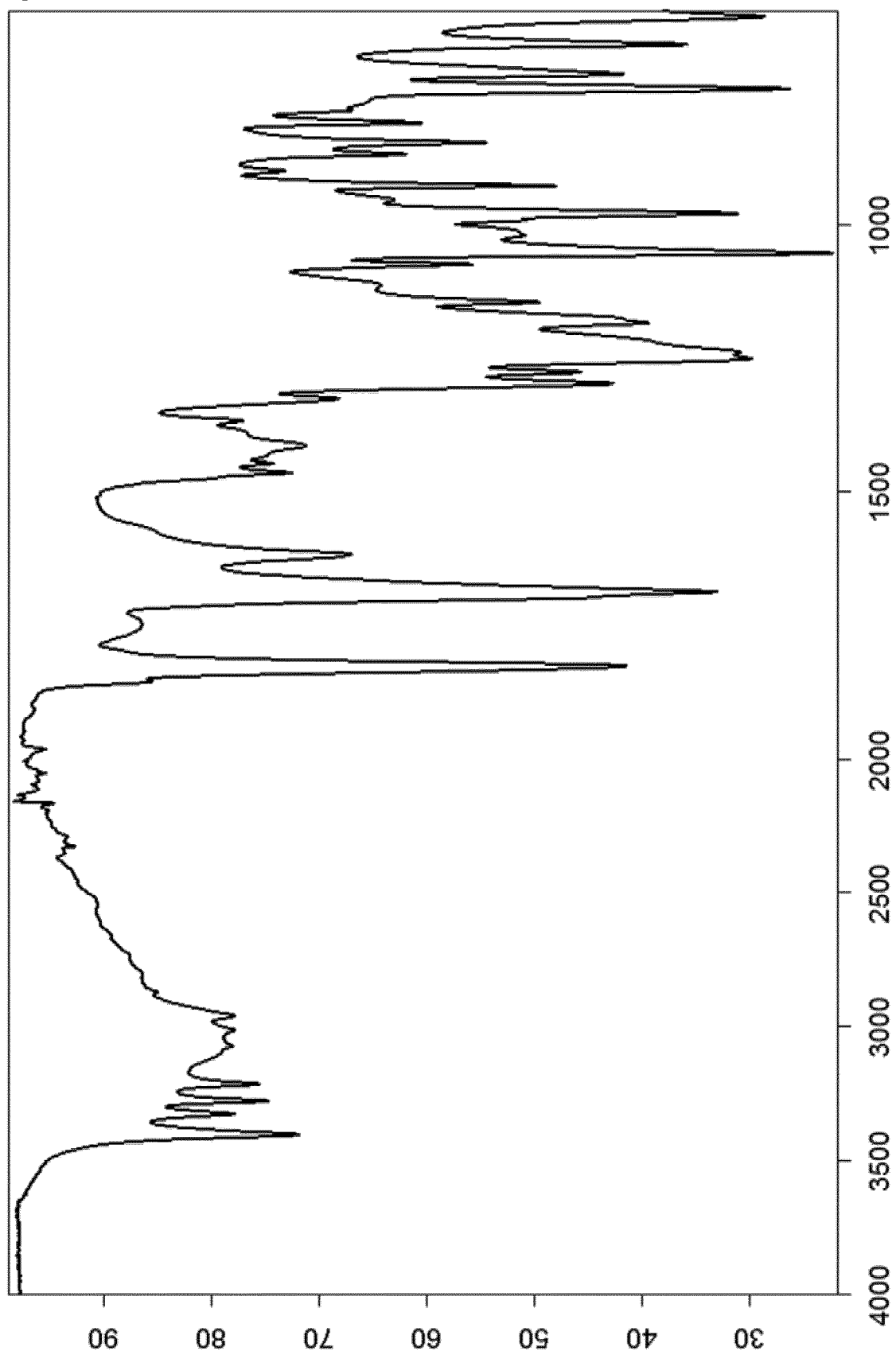
FIG. 7: illustrates a representative Fourier transform infrared spectrum in transmission mode of the crystalline form (Form 2) of avibactam according to the present invention. The x-axis shows the frequency in wavenumbers (cm$^{-1}$), the y-axis shows the relative intensity of the peaks in percent (%).

In one embodiment the present invention relates to a crystalline form (Form 2) of [(2S,5R)-2-carbamoyl-7-oxo-1,6-diazabicylco[3.2.1]octan-6-yl] hydrogen sulfate according to Formula (I) characterized by having a Fourier transform infrared spectrum essentially the same as the one displayed in FIG. 7 of the present invention, when measured with a diamond ATR cell.

In another embodiment, the present invention relates to a crystalline form of [(2S,5R)-2-carbamoyl-7-oxo-1,6-diazabicylco[3.2.1]octan-6-yl] hydrogen sulfate according to Formula (I) characterized by showing a weight loss of about 0.5 weight % or less, preferably of about 0.4 weight % or less, more preferably of about 0.3 weight % or less based on the weight of the crystalline form of avibactam, when measured with thermogravimetric analysis at a temperature in the range of from about 25 to 130° C. and a heating rate of about 10 K/min. Preferably, said crystalline form of [(2S,5R)-2-carbamoyl-7-oxo-1,6-diazabicylco[3.2.1]octan-6-yl] hydrogen sulfate is present in crystalline Form 1 of avibactam as defined above.

Figure 3:
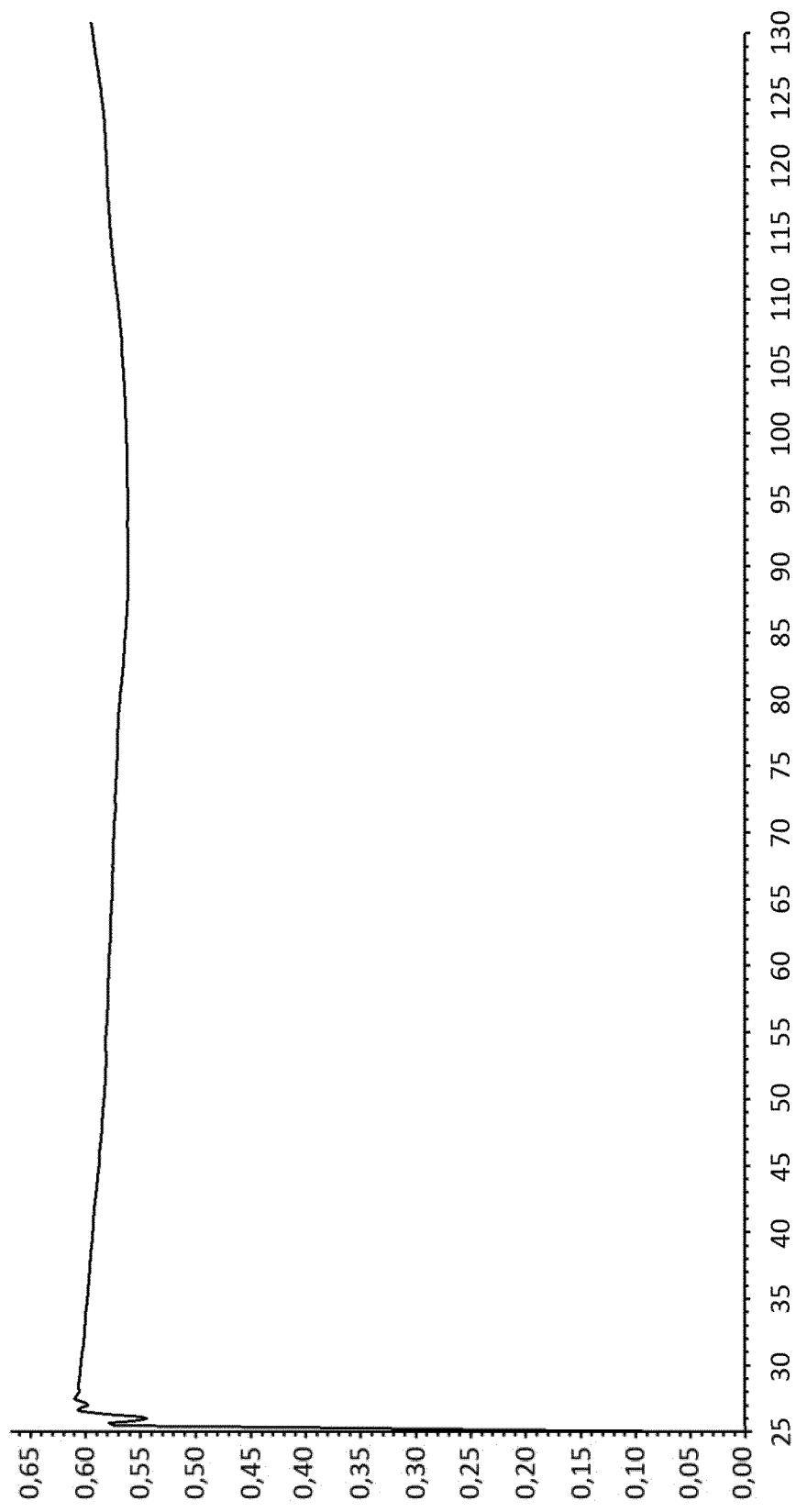
FIG. 3: illustrates a representative differential scanning calorimetry curve of the crystalline form (Form 1) of avibactam according to the present invention in the temperature range of from 25 to 130° C. The x-axis shows the temperature in degree Celsius (° C.), the y-axis shows the heat flow rate in Watt per gram (W/g) with endothermic peaks going up.
Figure 4:
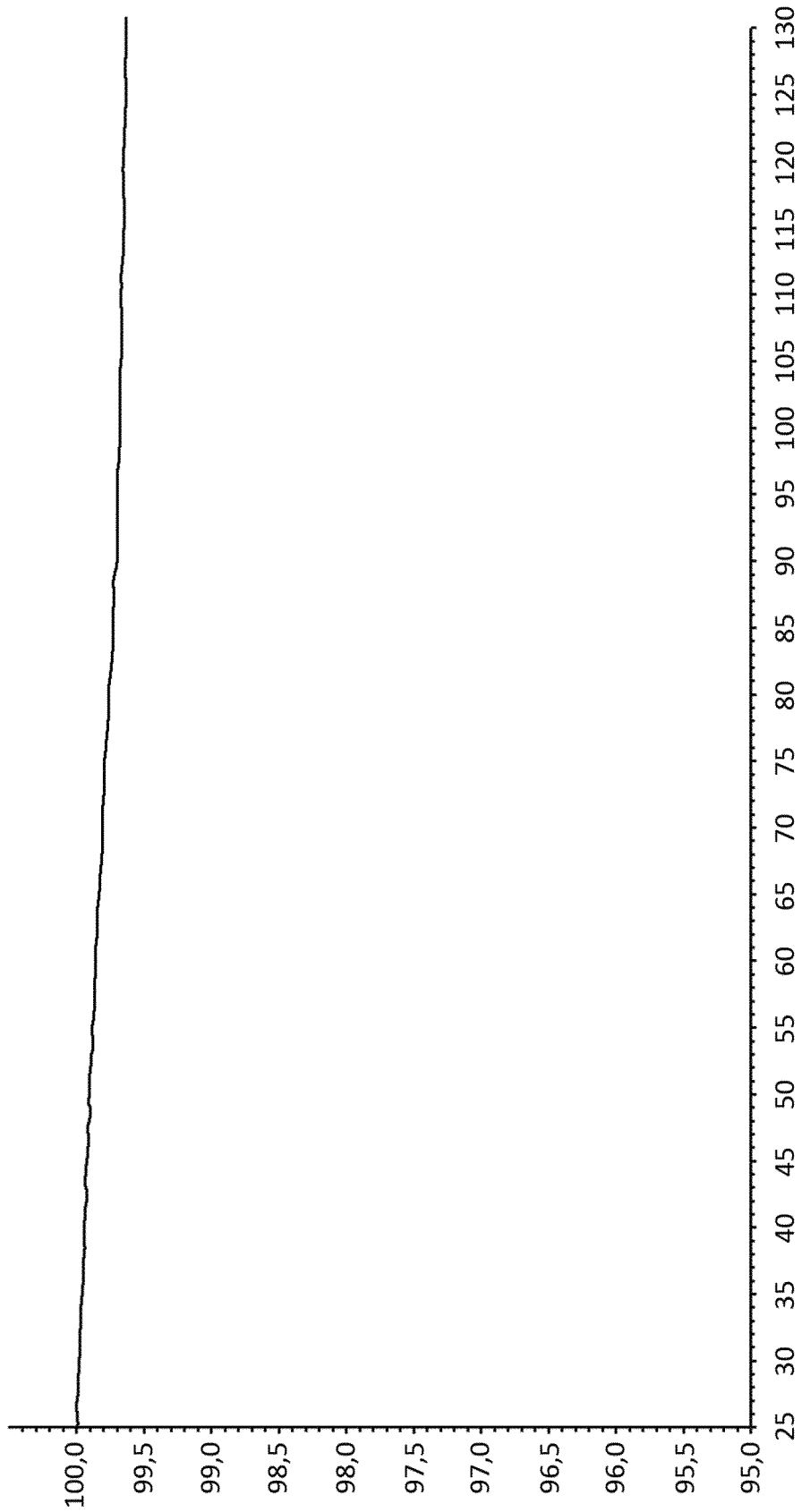
FIG. 4: illustrates a representative thermogravimetric analysis curve of the crystalline form (Form 1) of avibactam according to the present invention in the temperature range of from 25 to 130° C. The x-axis shows the temperature in degree Celsius (° C.), the y-axis shows the mass (loss) of the sample in weight percent (weight %).

Thermal analysis revealed that avibactam free acid of the present invention is very stable against temperature stress. For example, avibactam free acid of the present invention shows no thermal event in the differential scanning calorimetry curve up to a temperature of at least about 130° C. (see FIG. 3 herein), preferably up to a temperature of at least about 160° C. and most preferably up to a temperature of at least about 200° C. In addition, avibactam of the present invention shows a weight loss of only about 0.3 weight % up to a temperature of about 130° C., when measured with thermogravimetric analysis (see FIG. 4) indicating that avibactam free acid of the present invention is an anhydrous and non-solvated form of avibactam. In addition, avibactam free acid of the present invention is also very stable against moisture. These properties ensure a constant product quality throughout shelf-life since form conversions upon storage can be excluded.

Figure 5A:
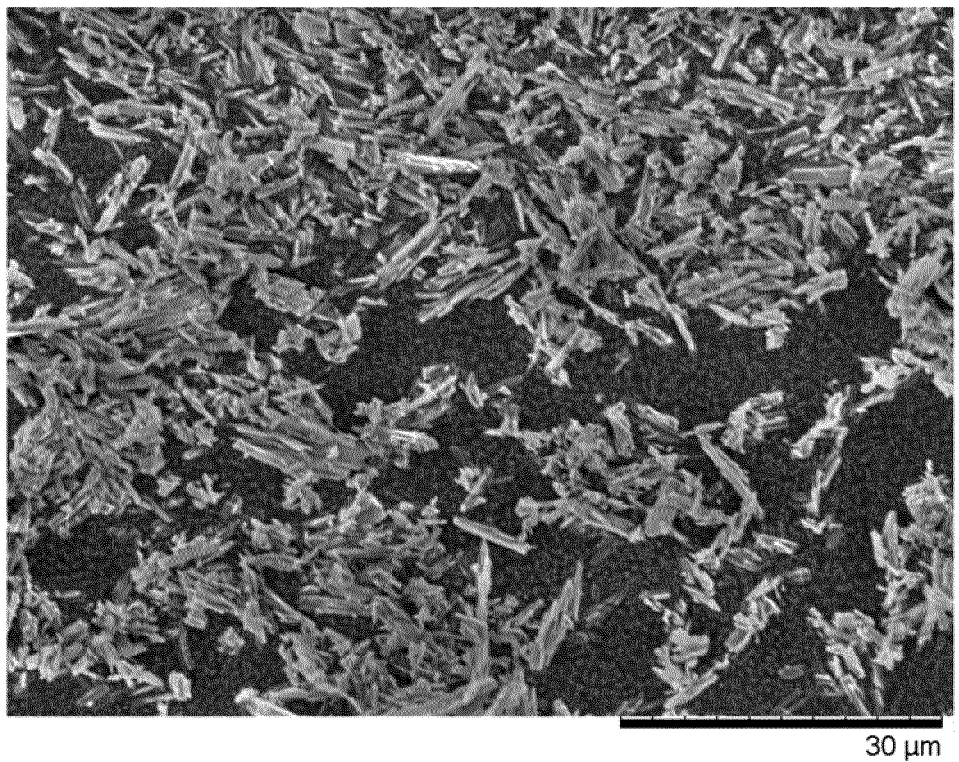
FIG. 5a: illustrates a scanning electron microscopic image of the crystalline form (Form 1) of avibactam according to the present invention.

Besides being stable against temperature and moisture stress avibactam free acid of the present invention is also characterized by excellent powder properties. As can be seen from the scanning electron microscopic image displayed in FIG. 5a herein avibactam free acid of the present invention mainly consists of lath-shaped crystals with a very homogenous particle size distribution resulting in a free-flowing powder with high bulk density and good compaction properties. Such powder properties are especially convenient for pharmaceutical processes including filling processes into containments, for example into vials e.g. single unit vials.

Figure 5B:
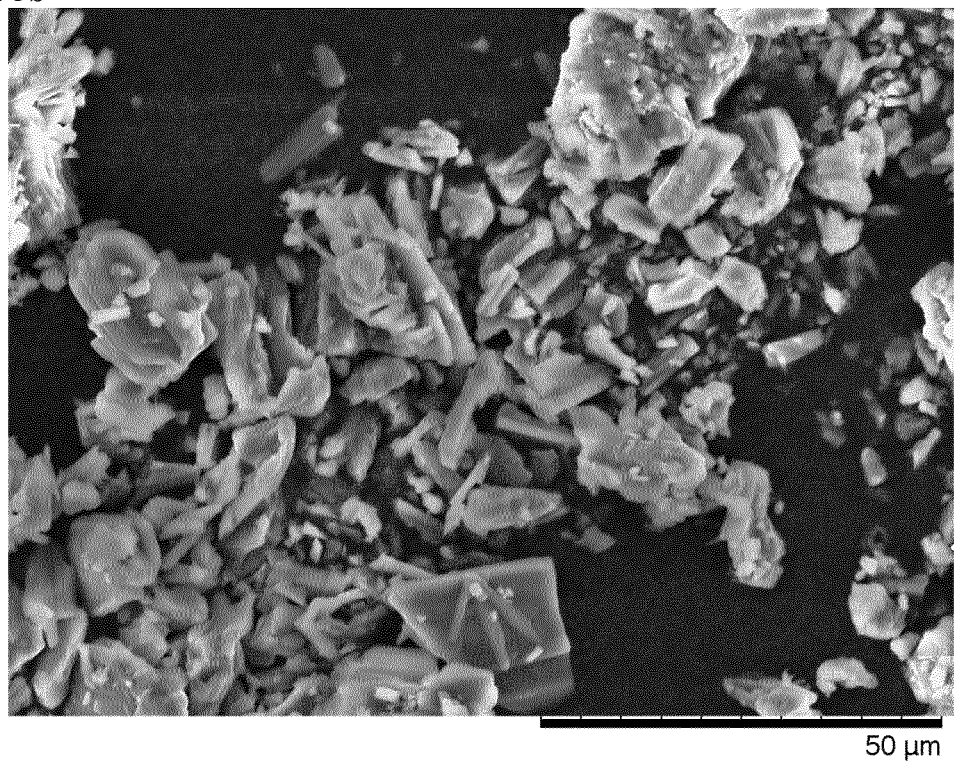
FIG. 5b: illustrates a scanning electron microscopic image of crystalline form B of avibactam sodium according to WO 2011/042560 A1.
Figure 5C:
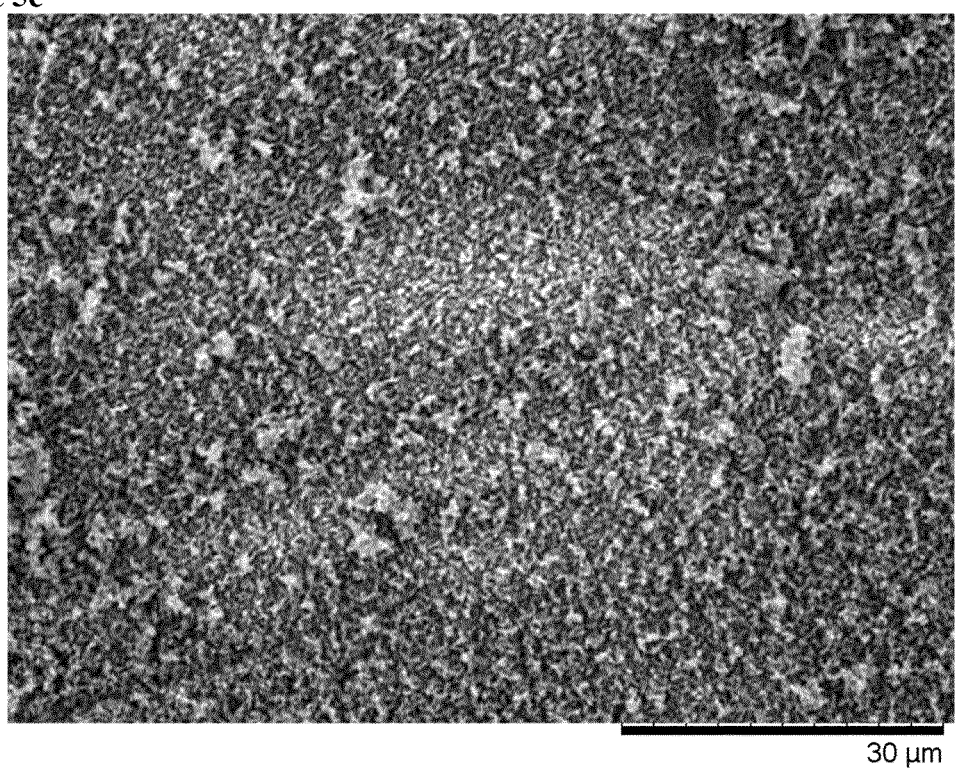
FIG. 5c: illustrates a scanning electron microscopic image of crystalline form D of avibactam sodium according to WO 2011/042560 A1.

Form B of avibactam sodium shows plate-like crystals with diverse particle sizes (see FIG. 5b herein). Finally, the statement provided in WO 2011/042560 A1, that anhydrous form D consists of very small crystals could be confirmed (see FIG. 5c). Such a powder is usually electrostatically charged and dusting and hence not preferred for pharmaceutical processing.

Furthermore, the invention relates to a method for the preparation of [(2S,5R)-2-carbamoyl-7-oxo-1,6-diazabicylco[3.2.1]octan-6-yl] hydrogen sulfate according to Formula (I) comprising:

(a) Reacting a Compound According to Formula (II)

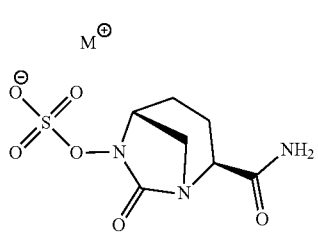

Formula (II)

wherein M⊕ is N⊕ RR'R"R''' with R, R', R" and R''' each being independently selected from hydrogen and alkyl with 1 to 6 carbon atoms, with one or more acid(s) having a pKa<−1; and (b) Optionally Isolating at least a part of the Compound According to Formula (I).

In the course of the present invention an alkyl group is a group comprising interconnected carbon and hydrogen atoms. An alkyl group can be a linear or a branched alkyl group.

Linear alkyl groups with 1 to 6 carbons can be methyl (—CH$_3$), ethyl (—CH$_2$CH$_3$), propyl (—(CH$_2$)$_2$CH$_3$), butyl (—(CH$_2$)$_3$CH$_3$), pentyl (—(CH$_2$)$_4$CH$_3$) and hexyl (—(CH$_2$)$_5$CH$_3$). In the present invention linear alkyl groups with 3 to 6 carbons may be indicated by using the prefix "n-" e.g. n-propyl, n-butyl, n-pentyl and n-hexyl.

Examples of branched alkyl groups are isopropyl (—CH(CH$_3$)$_2$), isobutyl (—CH$_2$CH(CH$_3$)$_2$), tert-butyl (—CH(CH$_3$)$_3$), isopentyl (—(CH$_2$)$_2$CH(CH$_3$)$_2$) and neohexyl (—(CH$_2$)$_2$CH(CH$_3$)$_3$).

In a preferred embodiment R, R', R" and R''' each are the same alkyl group. It is further preferred that R, R', R" and R''' each are a linear alkyl group, preferably the same linear alkyl group. In a particularly preferred embodiment R, R', R" and R''' each are n-butyl. Thus, it is particularly preferred that M⊕ is (Bu)$_4$N⊕.

In step (a) the compound according to Formula (II) is reacted with an acid having a pK$_a$ value<−1. The smaller the pK$_a$ value the stronger the acid. Acids having a pK$_a$ value<−1 can be regarded as strong acids.

The one or more acid(s) having a pKa<−1 is preferably selected from the group consisting of p-toluenesulfonic acid, p-toluenesulfonic acid monohydrate, p-xylene-2-sulfonic acid hydrate, benzenesulfonic acid, p-fluorobenzenesulfonic acid, 2,4,6-tri-methylbenzenesulfonic acid, camphor-10-sulfonic acid, nonafluorobutane-1-sulfonic acid, methanesulfonic acid, ethanesulfonic acid, 2-hydroxyethanesulfonic acid, n-propanesulfonic acid, n-butanesulfonic acid, n-hexanesulfonic acid, cyclopentane-sulfonic acid, trifluoromethanesulfonic acid, sulfuric acid, hydrochloric acid, hydro-bromic acid, hydroiodic acid, nitric acid and mixtures of one or more thereof. Particularly preferred acids are selected from the group of p-toluenesulfonic acid, p-toluenesulfonic acid monohydrate, hydrochloric acid and nitric acid. Especially preferred is p-toluenesulfonic acid monohydrate. Alternatively, particularly preferred is p-toluenesulfonic acid.

Phosphoric acid, trifluoroacetic acid and formic acid are preferably not used as acids.

In a preferred embodiment the compound according to Formula (II) and the acid are reacted in a molecular ratio in the range of from about 1:1 to 1:1.8, more preferably from about 1:1.01 to 1:1.6, even more preferably from about 1:1.02 to 1:1.4, in particular from about 1:1.03 to 1:1.15.

In a preferred embodiment, the reaction is carried out in a solvent selected from the group consisting of alcohols e.g. ethanol, n-propanol, isopropanol, isobutanol, 2-butanol, amylalcohol, methylene chloride, acetone, ethyl acetate, acetonitrile and mixtures thereof. Preferred solvents are methylene chloride, isobutanol, acetone and ethanol. Methylene chloride and ethanol are especially preferred. The solvent preferably comprises less than 2% w/w, more preferably less than 1% w/w, in particular less than 0.3% w/w of water. Especially preferred is when the solvent is substantially free of water.

It is further preferred that the reaction is carried out at a temperature in the range of from about −10° C. to 35° C., preferably from about −8° C. to 25° C., even more preferably from about −6° C. to 15° C., in particular from about −5° C. to 5° C.

The reaction can preferably be carried out for a period in the range of from about 5 to 240 minutes, preferably from about 10 to 180 minutes, more preferably from about 15 to 90 minutes, in particular from about 20 to 45 minutes.

Further, the reaction mixture is preferably subjected to agitation, mechanical agitation and/or stirring.

In optional step (b) at least part of the compound according to Formula (I) can be isolated.

Isolating the compound according to Formula (I) can preferably comprise filtering off the precipitate obtained in step (a). Filtering off the precipitate can for example be carried out with the aid of a suction device, a funnel with sieve bottom or filter paper. Further, the filtered precipitate can preferably be washed, preferably with the solvent in which the reaction of step (a) was carried out, in particular with methylene chloride or ethanol. Further, the compound according to Formula (I) can preferably be dried. Drying can preferably be carried out under reduced pressure in the range of from about 5 to 200 mbar. Further, drying can be carried out at a temperature in the range of from about 10° C. to 35° C., preferably at about room temperature.

It was unexpectedly found that the above described process yields avibactam free acid in high purity. For example, avibactam free acid having a purity of 97% was obtained, although the tetrabutylammonium salt starting material had a significantly lower purity of only about 76% (see also example 1.4 herein).

Therefore, the present invention also relates to [(2S,5R)-2-carbamoyl-7-oxo-1,6-diazabicylco[3.2.1]octan-6-yl] hydrogen sulfate according to Formula (I) having high purity of at least 95%, preferably of at least 97%, more preferably of at least 98% and most preferably of at least 99%, such as of at least 99.5% e.g. 100%. Preferably, said [(2S,5R)-2-carbamoyl-7-oxo-1,6-diazabicylco[3.2.1]octan-6-yl] hydrogen sulfate is present in crystalline Form 1 of avibactam as defined above. The purity may be determined by quantitative 1H-NMR as disclosed herein and/or by other analytical methods well known to the skilled person such as high performance liquid chromatography (HPLC) and mass spectrometry (MS) or any combinations thereof.

High purity is a prerequisite for an active pharmaceutical ingredient since by-products do not have the desired pharmacological activity and on top may be even toxic.

Hence, an additional subject-matter of the present invention relates to the use of avibactam free acid as defined hereinabove for the preparation of a pharmaceutical composition.

In a further aspect the present invention relates to a pharmaceutical composition comprising an effective and/or predetermined amount of avibactam free acid as defined hereinabove, one or more alkaline sodium salt(s) and one or more antibacterial agent(s).

The one or more alkaline sodium salt(s) is preferably selected from the group consisting of sodium carbonate ($Na_2CO_3$), sodium hydrogen carbonate ($NaHCO_3$), sodium acetate, sodium formiate and sodium benzoate, wherein sodium carbonate and sodium hydrogen carbonate are particular preferred and sodium carbonate is most preferred.

Preferably, the one or more antibacterial agent(s) is a beta-lactam antibiotic including penams, penems, cephems, carbacephems, oxacephems, cephamycins, penicillins such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin, pivampicillin, cephalosporins such as cephalothin, cephalorodine, cefaclor, cefadroxil, cefamandole, cefazoline, cephalexin, cephradine, ceftizoxime, cefmenoxime, cefmetazole, cephaloglycin, cefonicid, cefodizime, cefpirome, ceftazidime, ceftaroline, ceftaroline fosamil, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, carbapenems such as imipenem, meropenem, biapenem, panipenem and monobactams such as aztreonam and carumonam as well as salts thereof. Most preferably, the beta-lactam antibiotic is selected from ceftazidime e.g. in form of its pentahydrate and/or ceftarolin fosamil e.g. in form of its monoacetate monohydrate.

The pharmaceutical composition of the present invention as defined above may further comprise one or more pharmaceutically acceptable excipient(s).

The pharmaceutical composition of the invention can be prepared by successively filling the single components of the pharmaceutical composition as defined above into a containment for example into a vial e.g. a single unit vial.

In a preferred embodiment the pharmaceutical composition of the present invention as defined above is a sterile powder for injection, preferably comprised in a single-use vial. Before application to a patient in need the powder may be reconstituted for example with sterile water for injection, 0.9% sodium chloride, 5% dextrose, 2.5% dextrose/0.45% sodium chloride or Lactated Ringer's solution optionally followed by further dilution with a suitable infusion fluid.

In a further aspect the present invention concerns the pharmaceutical composition as defined above for use as medicament.

Another aspect of the present invention relates to the pharmaceutical composition as defined above for the treatment and/or prevention of bacterial infections. The bacterial infections may be caused by beta-lactamase producing bacteria. The bacterial infection may be selected from complicated intra-abdominal infections (cIAI) and complicated urinary tract infections (cUTI).

As already mentioned above avibactam free acid of the present invention is obtained in high purity when prepared according to the aforementioned process and therefore may also be advantageously used as intermediate for the production of pure avibactam sodium.

Hence, in a further aspect the invention also relates to the use of [(2S,5R)-2-carbamoyl-7-oxo-1,6-diazabicylco[3.2.1]octan-6-yl] hydrogen sulfate according to Formula (I) as defined hereinbefore for the preparation of an avibactam salt, in particular for the preparation of avibactam sodium.

Another aspect of the invention is a method for the preparation of the compound according to Formula (III)

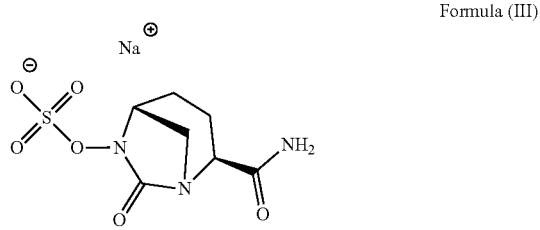 [SMILES: [Na+] ; NC(=O)[C@@H]1CC[C@@H]2CN1C(=O)N2OS(=O)(=O)[O-]]

Formula (III)

comprising
(i) reacting [(2S,5R)-2-carbamoyl-7-oxo-1,6-diazabicylco[ 3.2.1]octan-6-yl] hydrogen sulfate according to Formula (I) with one or more sodium salt(s) of an organic acid having 2 to 8 carbon atoms; and
(ii) optionally isolating at least a part of the compound according to Formula (III).

The starting material [(2S,5R)-2-carbamoyl-7-oxo-1,6-diazabicylco[3.2.1]octan-6-yl] hydrogen sulfate according to Formula (I) can be prepared by the method described hereinabove for avibactam free acid preparation.

In the context of the method for the preparation of the compound according to Fomula (III) the term "organic acid" refers to an organic compound having a carboxylic acid group. An organic compound can be referred to as a compound, which apart from carbon, hydrogen and oxygen atoms further substantially contains nitrogen, halogens and sulfur atoms. A carboxylic acid group is a group which can be represented by the following Formula

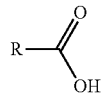

Thus, a carboxylic acid group is a group in which a carbon atom is connected by a covalent double bond to one oxygen atom and by a further bond to another oxygen atom further otherwise bonded to a hydrogen atom. The sodium salt of an organic acid can be referred to as a carboxylic acid group in which the the hydrogen atom connected to the oxygen of the carboxylic acid group is substituted by sodium.

In a preferred embodiment the organic acid having 2 to 8 carbon atoms consists of carbon, hydrogen and oxygen atoms.

The organic acid can have more than one carboxylic acid groups, for example two carboxylic acid groups like in the case of oxalic acid. However, it is preferred that the organic acid comprises just one single carboxylic acid group.

Examples of an organic acid with 2 to 8 carbon atoms, wherein the organic acid comprises one carboxylic acid group, are acetic acid, propanoic acid, butyric acid, pivalic acid, hexanoic acid, 2-ethyl hexanoic acid and octanoic acid.

It is preferred that the organic acid has 4 to 8 carbon atoms, more preferably 6 to 8 carbon atoms.

In a particularly preferred embodiment the organic acid is hexanoic acid. The corresponding sodium salt is referred to as sodium hexanoate.

In an alternative particularly preferred embodiment the organic acid is 2-ethylhexanoic acid. The corresponding sodium salt is referred to as sodium 2-ethylhexanoate.

In a preferred embodiment the compound according to Formula (I) and the sodium salt of an organic acid having 2 to 8 carbon atoms are reacted in a molecular ratio in the range of from about 1:1.3 to 1:2.5, more preferably from about 1:1.4 to 1:2.4, even more preferably from about 1:1.6 to 1:2.3, in particular from about 1:1.8 to 1:2.2. The molecular ratio is determined on the basis of the number of sodium carboxylate groups of the organic acid. Thus, in case that, for example, disodium salt of the hexanedioic acid is submitted to the reaction with the compound according to Formula (I) the molar amount of the organic acid is halved compared to the monosodium salt of an organic acid with one carboxy group such as hexanoic acid. The molecular ratio of the compound according to Formula (I) and the disodium salt of the hexanedioic acid is accordingly in the range of from about 1:0.65 to 1:1.25, more preferably from about 1:0.7 to 1:1.2, even more preferably from about 1:0.8 to 1:1.15, in particular in the range of from about 1:0.9 to 1:1.1.

In a preferred embodiment, the reaction is carried out in an organic solvent, preferably an organic solvent having a boiling point in the range of from about 60 to 135° C. at 1.013 bar. Examples of organic solvents are ethanol, n-propanol, isopropanol, n-butanol isobutanol, 2-butanol, isoamylalcohol, 2-methyl-2-butanol, ethyl acetate, acetonitrile and mixtures thereof. Preferred are isopropanol, isobutanol and 2-butanol. Isobutanol is especially preferred. The solvent preferably comprises less than 5% w/w, more preferably less than 3% w/w, in particular less than 0.5% w/w of water. Especially preferred is when the solvent is substantially free of water.

It is further preferred that the reaction is carried out at a temperature in the range of from about 60° C. to 135° C., preferably from about 75° C. to 130° C., in particular from about 85° C. to 125° C. For example, the reaction may be carried out at a temperature in the range of from about 90° C. to 115° C., especially when isobutanol or 2-butanol is used as solvent.

The reaction can preferably be carried out for a period in the range of from about 5 to 240 minutes, preferably from about 10 to 180 minutes, more preferably from about 20 to 120 minutes, in particular from about 30 to 90 minutes.

Further, the reaction mixture is preferably subjected to agitation, mechanical agitation and/or stirring.

In optional step (ii) at least part of the compound according to Formula (III) can be isolated.

Isolating the compound according to Formula (III) can preferably comprise cooling the reaction mixture of step (i) for example to a temperature in the range of from about −10° C. to 23° C., preferably from about −7° C. to 15° C., in particular from about −5° C. to 10° C. In a preferred embodiment cooling the reaction mixture of step (i) can preferably be carried out under mechanical movement, such as stirring.

In a preferred embodiment optional step (ii) can preferably comprise filtering off the precipitate obtained in step (i) or the precipitate may be filtered off after cooling as mentioned above. Filtering off the precipitate can for example be carried out with the aid of a suction device, a funnel with sieve bottom or filter paper. Further, the filtered precipitate can preferably be washed, preferably with the solvent in which the reaction of step (i) was carried out, in particular with isobutanol. Further, the compound according to Formula (III) can preferably be dried. Drying can be preferably carried out under reduced pressure in the range of from about 5 to 200 mbar. Further, drying can be carried out at a temperature in the range of from about 10 to 35° C., preferably at about room temperature.

According to the above described method the compound according to Formula (III) may be obtained in amorphous form, crystalline form or as a mixture of amorphous and crystalline forms, preferably it is obtained in crystalline form. When obtained in crystalline form, the compound according to Formula (III) is preferably present in crystalline form A, form B, form C, form D or mixtures thereof. Most preferably, the compound according to Formula (III) is obtained as crystalline form C.

In a preferred embodiment the method for the preparation of the compound according to Formula (III)

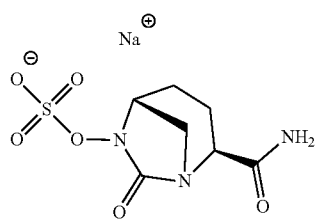

Formula (III)

comprises
(i) reacting [(2S,5R)-2-carbamoyl-7-oxo-1,6-diazabicylco[3.2.1]octan-6-yl] hydrogen sulfate according to Formula (I) with sodium ethylhexanoate in water-free isobutanol under reflux, and
(ii) optionally isolating at least a part of the compound according to Formula (III), in particular the compound according to Formula (III) in crystalline form C.

Generally, as far as the further conditions in step (i) and optional step (ii) are concerned, the same applies as described above.

EXAMPLES

The following analytical methods and parameters have been applied for the generation of analytical data disclosed in the present invention:

Powder X-Ray Diffraction

Powder X-ray diffraction was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions. Diffractograms were measured at room temperature. A typical precision of the 2-Theta values is in the range of ±0.2° 2-Theta. Thus, the diffraction peak of the crystalline form of avibactam of the present invention that appears for example at 17.4° 2-Theta can appear between 17.2 and 17.6° 2-Theta on most X-ray diffractometers under standard conditions.

Fourier Transform Infrared Spectroscopy

Fourier transform infrared spectroscopy (FTIR) was performed with a MKII Golden Gate™ Single Reflection Diamond ATR (attenuated total reflection) cell with a Bruker Tensor 27 FTIR spectrometer with 4 cm$^{-1}$ resolution. Spectra were recorded at room temperature. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^1$. Thus, the infrared peak of the crystalline form of avibactam of the present invention that appears at 1820 cm$^1$ can appear between 1818 and 1822 cm$^{-1}$ on most infrared spectrometers under standard conditions.

Differential Scanning Calorimetry

Differential scanning calorimetry was performed on a Mettler Toledo Polymer DSC R instrument. The sample (1.27 mg) was heated in a 40 microL aluminium pan with pierced aluminium lid from 25 to 160° C. at a rate of 10 K/min. Nitrogen (purge rate 50 mL/min) was used as purge gas.

Thermogravimetric Analysis

Thermogravimetric analysis (TGA) was performed on a Mettler TGA/DSC 1 instrument. The sample (6.30 mg) was heated in a 100 microL aluminum pan closed with an aluminum lid. The lid was automatically pierced at the beginning of the measurement. The sample was heated from 25 to 200° C. at a rate of 10 K/min. Nitrogen (purge rate 50 mL/min) was used as purge gas.

Scanning Electron Microscopy

Scanning electron microscopic images were recorded with a Hitachi TM3030Plus Tabletop scanning electron microscope. The samples were prepared on a carbon disk and observed in a mixed secondary electron/back scattering electron (SE/BSE) mode with charge-up reduction applying an accelerating voltage of 5 kV.

Nuclear Magnetic Resonance

Nuclear magnetic resonance spectra were acquired on a Bruker 400 MHz spectrometer. Chemical shifts δ are expressed as parts per million (ppm) and were referenced to residual solvent signals at 2.50 ppm (DMSO-D6) for the proton NMR spectra as well as to the solvent signal 39.52 ppm (DMSO-D6) for 13C NMR spectra. Coupling constants are quoted in Hz. TCNB (2,3,5,6-tetrachloronitrobenzene) was used as internal standard for quantitative 1H-NMR measurements.

The following non-limiting examples are illustrative for the disclosure.

Example 1: Preparation of [(2S,5R)-2-carbamoyl-7-oxo-1,6-diazabicylco[3.2.1]octan-6-yl] Hydrogen Sulfate (Avibactam)

Example 1.1

Avibactam tetrabutylammonium salt (255 mg, 0.50 mmol, prepared according to the procedure disclosed in example 4a of U.S. Pat. No. 8,969,566 B2) was dissolved in 2.5 mL ethanol and cooled to 0-5° C. Under stirring p-toluenesulfonic acid monohydrate (102 mg, 0.53 mmol) was added and a white precipitate formed. After stirring for 30 min at 0-5° C., the solid was filtered off, washed with ethanol and dried under vacuum at room temperature to yield 90 mg of avibactam free acid in polymorphic Form 1 (Yield: 68%, Purity: 100% by QNMR).

1H-NMR (400 MHz, DMSO-D6), δ[ppm]: 7.44 (bs, 1H, NH$_{amide}$), 7.29 (bs, 1H, NH$_{amide}$), 6.97 (bs, SO$_3$H), 3.98 (s, 1H, CH), 3.69 (d, J=5.1 Hz, 1H, CH), 3.03 (d, J=10.5 Hz, 1H, CH$_2$), 2.93 (d, J=11.4 Hz, 1H, CH$_2$), 2.13-1.98 (m, 1H, CH$_2$), 1.91-1.75 (m, 1H, CH$_2$) 1.72-1.54 (m, 2H, CH$_2$)

$^{13}$C-NMR (400 MHz, DMSO-D6), δ[ppm]: 171.5, 165.8, 59.6, 57.5, 47.0, 20.5, 18.1

The powder X-ray diffractogram of the obtained material is displayed in FIG. 1 and the corresponding reflection list is provided in table 1.

TABLE 1

Reflections in the range of 2.0 to 30.0° 2-Theta and corresponding relative intensities

| Angle [±0.2 °2-Theta] | Relative Intensity [%] |
|---|---|
| 9.6 | 7 |
| 11.1 | 16 |
| 14.2 | 2 |
| 16.4 | 25 |
| 16.7 | 8 |
| 17.4 | 100 |
| 19.2 | 15 |
| 19.7 | 3 |
| 20.2 | 6 |
| 20.8 | 3 |
| 21.8 | 3 |
| 22.1 | 21 |
| 22.4 | 11 |
| 23.5 | 4 |
| 24.2 | 19 |
| 24.8 | 2 |
| 25.6 | 1 |
| 26.2 | 4 |
| 26.8 | 3 |
| 27.7 | 3 |
| 28.3 | 8 |
| 29.1 | 5 |

The Fourier transform infrared spectrum of the obtained material is displayed in FIG. 2 and the corresponding peak list is provided in table 2.

TABLE 2

FTIR peaks in the range of 4000 and 600 cm$^{-1}$
Wavenumber
[±2 cm$^{-1}$]

| |
|---|
| 3391 |
| 3326 |
| 3274 |
| 3214 |
| 3120 |
| 2966 |
| 1820 |
| 1688 |
| 1619 |
| 1466 |
| 1447 |
| 1408 |
| 1373 |
| 1304 |
| 1275 |
| 1241 |
| 1176 |
| 1143 |
| 1109 |
| 1074 |
| 1054 |
| 1021 |
| 977 |
| 927 |
| 898 |
| 867 |
| 848 |
| 810 |
| 787 |
| 743 |
| 723 |
| 662 |
| 608 |

Example 1.2

Avibactam tetrabutylammonium salt (250 mg, 0.49 mmol, prepared according to the procedure disclosed in example 4a of U.S. Pat. No. 8,969,566 B2) was dissolved in methylene chloride (2.5 mL) and cooled to 0-5° C. Under stirring HNO$_3$ (65%, 33 microL, 0.51 mmol) was added. After stirring for 30 min at 0-5° C., the white precipitate formed was filtered off, washed with methylene chloride (1 mL) and dried under vacuum at room temperature to yield 79 mg of avibactam in form of the free acid (Yield: 60%, Purity: 100% by QNMR)

Example 1.3

Avibactam tetrabutylammonium salt (250 mg, 0.49 mmol, prepared according to the procedure disclosed in example 4a of U.S. Pat. No. 8,969,566 B2) was dissolved in methylene chloride (2.5 mL) and cooled to 0-5° C. Under stirring conc. HCl (37%; 42 microL, 0.51 mmol) was added. After stirring for 30 min at 0-5° C., the white precipitate formed was filtered off, washed with methylene chloride (1 mL) and dried under vacuum at room temperature to yield 75 mg of avibactam in form of the free acid (Yield: 55%, Purity: 97% by QNMR).

Example 1.4: Purification Effect

Avibactam tetrabutylammonium salt (2.0 g, Purity: 76% by QNMR, 3.00 mmol, prepared according to the procedure disclosed in example 4a of U.S. Pat. No. 8,969,566 B2) was dissolved in methylene chloride (20 mL) and cooled to 0-5° C. Under stirring p-toluenesulfonic acid monohydrate (0.80 g, 4.15 mmol) was added and a white precipitate formed. After stirring for 30 min at 0-5° C., the solid was filtered off, washed with methylene chloride and dried under vacuum at room temperature to yield 0.73 g (Yield: 89%, Purity: 97% by QNMR).

Example 1.5

Avibactam tetrabutylammonium salt (251 mg, 0.49 mmol, prepared according to the procedure disclosed in example 4a of U.S. Pat. No. 8,969,566 B2) was dissolved in 4.0 mL isobutanol and cooled to 0-5° C. Under stirring p-toluenesulfonic acid monohydrate (105 mg, 0.53 mmol) was added and a white precipitate formed. After stirring for 30 min at 0-5° C., the solid was filtered off, washed with isobutanol and dried under vacuum at room temperature to yield 115 mg of avibactam free acid in polymorphic Form 2 (Yield: 87%, Purity: 92% by QNMR).

1H-NMR (400 MHz, DMSO-D6), δ[ppm]: 7.45 (bs, 1H, NH$_{amide}$), 7.26 (bs, 1H, NH$_{amide}$), 6.97 (bs, 5O$_3$H), 3.98 (s, 1H, CH), 3.70 (d, J=5.1 Hz, 1H, CH), 3.03 (d, J=10.5 Hz, 1H, CH$_2$), 2.93 (d, J=11.4 Hz, 1H, CH$_2$), 2.13-1.98 (m, 1H, CH$_2$), 1.91-1.75 (m, 1H, CH$_2$) 1.72-1.54 (m, 2H, CH$_2$)

The powder X-ray diffractogram of the obtained material is displayed in FIG. 6 and the corresponding reflection list is provided in table 3.

TABLE 3

Reflections in the range of 2.0 to 30.0° 2-Theta and corresponding relative intensities

| Angle [±0.2 °2-Theta] | Relative Intensity [%] |
|---|---|
| 9.3 | 30 |
| 10.1 | 36 |
| 13.4 | 3 |
| 16.3 | 40 |
| 16.7 | 100 |
| 18.8 | 46 |
| 19.5 | 19 |
| 20.3 | 4 |
| 21.8 | 4 |
| 23.0 | 15 |
| 24.4 | 22 |
| 24.8 | 5 |
| 25.7 | 13 |
| 26.8 | 4 |
| 29.6 | 9 |

The Fourier transform infrared spectrum of the obtained material is displayed in FIG. 7 and the corresponding peak list is provided in table 4.

TABLE 4

FTIR peaks in the range of 4000 and 600 cm$^{-1}$
Wavenumber [±2 cm$^{-1}$]

| |
|---|
| 3403 |
| 3326 |
| 3277 |
| 3214 |
| 2958 |
| 1825 |
| 1686 |
| 1616 |
| 1464 |
| 1413 |
| 1325 |
| 1297 |
| 1276 |
| 1251 |
| 1184 |
| 1145 |
| 1074 |
| 1053 |
| 979 |
| 927 |
| 868 |
| 846 |
| 809 |
| 746 |
| 718 |
| 663 |
| 611 |

Comparative Example 1

To a stirred solution of avibactam tetrabutylammonium salt (20.0 g, purity: 76% by QNMR, 30.0 mmol, prepared according to the procedure disclosed in example 4a of U.S. Pat. No. 8,969,566 B2) in ethanol (126 mL) a solution of sodium 2-ethylhexanoate (13.12 g, 78.9 mmol) in ethanol was added at 30° C. over five hours. The solution was seeded twice with avibactam sodium polymorphic form B (prepared according to the procedure disclosed in WO 2011/042560 A1) during addition of the sodium 2-ethylhexanoate solution. The suspension was stirred an additional 12 hours at 30° C. Subsequently the suspension was cooled to 0° C. for 2 hours, filtered and washed with ethanol at 0-5° C. The crystals were dried under reduced pressure at 25° C. for 18 hours and 7.45 g of avibactam sodium polymorphic form B was obtained (Purity: 74% by QNMR, Yield: 64%)

Reference Example 1

Avibactam tetrabutylammonium salt (100 mg, 0.197 mmol, prepared according to the procedure disclosed in example 4a of U.S. Pat. No. 8,969,566 B2) was dissolved in methylene chloride (1 mL) and cooled to 0-5° C. Under stirring trifluoroacetic acid (18 microL, 0.237 mmol) was added. The solution neither became turbid nor a solid precipitated.

Example 2: Synthesis of the Sodium Salt of [(2S, 5R)-2-carbamoyl-7-oxo-1,6-diazabicylco[3.2.1]octan-6-yl] Hydrogen Sulfate (Avibactam Sodium)

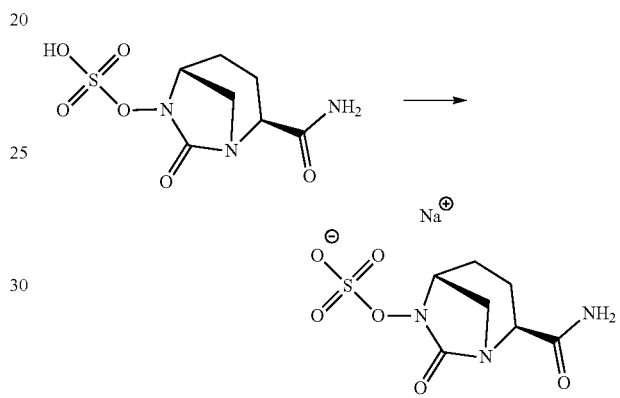

Example 2.1

Avibactam free acid (100 mg, 0.377 mmol, prepared according to one of the procedures described under example 1 herein) was suspended in isobutanol (2 mL). The suspension was heated under stirring to reflux temperature and a solution of sodium 2-ethylhexanoate (126 mg, 0.754 mmol) in isobutanol (2 mL) was added within 20 seconds. After refluxing the reaction mixture for 50 min, the suspension was cooled in an ice bath, the white solid was filtered off and washed with isobutanol to yield (84 mg, Yield: 77%) of avibactam sodium. Powder X-ray diffraction confirmed that avibactam sodium form C was obtained.

Example 2.2

Avibactam free acid (100 mg, 0.377 mmol, prepared according to one of the procedures described under example 1 herein) was suspended in isobutanol (2 mL). A solution of sodium ethylhexanoate (63 mg, 0.377 mmol) in isobutanol (2 mL) was added within 30 min under stirring. After, the suspension was stirred at room temperature overnight (approximately 16 hours), the white solid was filtered off and washed with isobutanol to obtain (32 mg, Yield: 29%) of avibactam sodium. Powder X-ray diffraction confirmed that avibactam sodium form D was obtained.

Example 2.3

Avibactam free acid (100 mg, 0.377 mmol, prepared according to one of the procedures described under example 1 herein) was suspended in a mixture of isobutanol (2 mL) and methanol (2 mL). The suspension was heated under stirring (oil bath temperature: 80° C.) and a solution of sodium 2-ethylhexanoate (126 mg, 0.754 mmol) in isobutanol (2 mL) was added within 20 seconds. After the suspension was stirred at 80° C. overnight (approximately 16 hours), the reaction vessel was cooled in an ice bath, the white solid was filtered off and washed with isobutanol to yield (65 mg, Yield: 60%) of avibactam sodium. Powder X-ray diffraction confirmed that avibactam sodium form B was obtained.

Reference Example 2

Avibactam free acid (100 mg, 0.38 mmol, prepared according to one of the procedures described in example 1 herein) was suspended in isobutanol (2 mL). The suspension was heated under stirring to reflux and a solution of sodium ethylhexanoate (63 mg, 0.38 mmol) in isobutanol (2 mL) was added within 60 seconds. A yellow suspension was formed within 7 minutes. After 2 hours, the solid was filtered off and washed. A composition containing avibactam sodium and undefined degradation products was obtained.

The invention claimed is:

1. A crystalline form of [(2S,5R)-2-carbamoyl-7-oxo-1,6-diazabicyclo[3.2.1]octan-6-yl] hydrogen sulfate according to Formula (I)

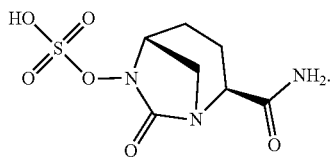

Formula (I)

characterized by
a powder X-ray diffractogram comprising reflections at 2-Theta angles of (9.6±0.2°), (11.1±0.2°) and (17.4±0.2°) or,
a powder X-ray diffractogram comprising reflections at 2-Theta angles of (9.3±0.2°), (10.1±0.2°) and (16.7±0.2°),
when measured with CuKalpha1,2 radiation having a wavelength of 0.15419 nm.

2. The crystalline form of [(2S,5R)-2-carbamoyl-7-oxo-1,6-diazabicyclo[3.2.1]octan-6-yl] hydrogen sulfate according to claim 1 characterized by
(i) having a powder X-ray diffractogram comprising reflections at 2-Theta angles of (9.6±0.2°), (11.1±0.2°) and (17.4±0.2°), when measured with CuKalpha$_{1,2}$ radiation having a wavelength of 0.15419 nm; and/or
(ii) having a Fourier transform infrared spectrum comprising peaks at wavenumbers of (3391±2) cm$^{-1}$, (1820±2) cm$^{-1}$ and (1688±2) cm$^{-1}$, when measured with a diamond ATR cell.

3. The crystalline form of [(2S,5R)-2-carbamoyl-7-oxo-1,6-diazabicyclo[3.2.1]octan-6-yl] hydrogen sulfate according to claim 1 characterized by
(i) having a powder X-ray diffractogram comprising reflections at 2-Theta angles of (9.3±0.2°), (10.1±0.2°) and (16.7±0.2°), when measured with CuKalpha$_{1,2}$ radiation having a wavelength of 0.15419 nm; and/or
(ii) having a Fourier transform infrared spectrum comprising peaks at wavenumbers of (3403±2) cm$^{-1}$, (1825±2) cm$^{-1}$ and (1686±2) cm$^{-1}$, when measured with a diamond ATR cell.

4. The crystalline form of [(2S,5R)-2-carbamoyl-7-oxo-1,6-diazabicyclo[3.2.1]octan-6-yl] hydrogen sulfate according to Formula (I) according to claim 1 having a purity of at least 95%.

5. A method for the preparation of the crystalline form of [(2S,5R)-2-carbamoyl-7-oxo-1,6-diazabicyclo[3.2.1]octan-6-yl] hydrogen sulfate according to Formula (I) as defined in claim 1 comprising:
(a) reacting a compound according to Formula (II)

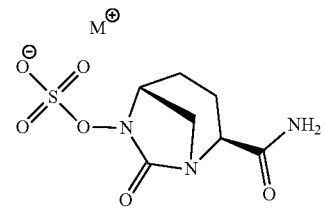

Formula (II)

wherein $M^{\oplus}$ is $N^{\oplus}RR'R''R'''$ with R, R', R" and R'" each being independently selected from hydrogen and an alkyl group with 1 to 6 carbon atoms,
with one or more acid(s) having a pKa<−1; and
(b) optionally isolating at least a part of the compound according to Formula (I).

6. The method according to claim 5, wherein $M^{\oplus}$ is $N^{\oplus}RR'R''R'''$ with R, R', R" and R'" each being n-butyl.

7. The method according to claim 5, wherein the acid having a pKa<−1 is selected from the group consisting of hydrochloric acid, nitric acid and p-toluene sulfonic acid.

8. A pharmaceutical composition comprising a solid crystalline form of [(2S,5R)-2-carbamoyl-7-oxo-1,6-diazabicyclo[3.2.1]octan-6-yl] hydrogen sulfate according to Formula (I)

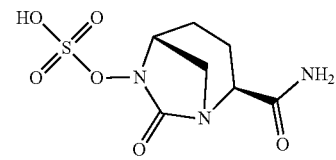

Formula (I)

characterized by
a powder X-ray diffractogram comprising reflections at 2-Theta angles of (9.6±0.2°), (11.1±0.2°) and (17.4±0.2°) or,
a powder X-ray diffractogram comprising reflections at 2-Theta angles of (9.3±0.2°), (10.1±0.2°) and (16.7±0.2°),
when measured with CuKalpha1,2 radiation having a wavelength of 0.15419 nm.

9. A pharmaceutical composition comprising an effective and/or predetermined amount of the solid crystalline form of [(2S,5R)-2-carbamoyl-7-oxo-1,6-diazabicyclo[3.2.1]octan-6-yl] hydrogen sulfate according to Formula (I) as defined in claim 1, one or more alkaline sodium salt(s) and one or more beta-lactam antibiotics selected from the group consisting of ceftazidime, ceftaroline fosamil and piperacillin.

10. The pharmaceutical composition according to claim 9, wherein the one or more alkaline sodium salt(s) is selected from sodium carbonate and sodium hydrogen carbonate.

11. The pharmaceutical composition according to claim 9, wherein the one or more beta-lactam antibiotics is selected from the group consisting of ceftazidime and piperacillin.

12. A method for treating bacterial infections comprising administering an effective amount of the crystalline form of [(2S,5R)-2-carbamoyl-7-oxo-1,6-diazabicyclo[3.2.1]octan-6-yl] hydrogen sulfate according to claim 1.

13. A method for preparing the compound according to Formula (III)

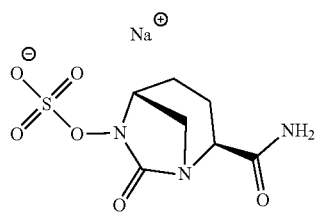

Formula (III)

comprising
(a) reacting a crystalline form of [(2S,5R)-2-carbamoyl-7-oxo-1,6-diazabicyclo[3.2.1]octan-6-yl] hydrogen sulfate according to Formula (I)

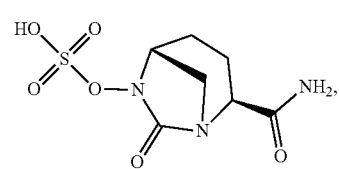

Formula (I)

characterized by a powder X-ray diffractogram comprising reflections at 2-Theta angles of (9.6±0.2°), (11.1±0.2°) and (17.4±0.2°) or, a powder X-ray diffractogram comprising reflections at 2-Theta angles of (9.3±0.2°), (10.1±0.2°) and (16.7±0.2°), when measured with CuKalpha1,2 radiation having a wavelength of 0.15419 nm, with one or more sodium salt(s) of an organic acid having 2 to 8 carbon atoms; and (b) optionally isolating at least a part of the compound according to Formula (III).

14. The method according to claim 13, wherein the sodium salt of the organic acid having 2 to 8 carbon atoms is sodium 2-ethylhexanoate.

* * * * *